United States Patent [19]

Kemner et al.

[11] 4,051,377
[45] Sept. 27, 1977

[54] SCANNING X-RAY EXAMINATION APPARATUS

[75] Inventors: Rudolf Kemner; Frans Wessel Zonneveld, both of Eindhoven, Netherlands

[73] Assignee: U.S. Philips Corporation, New York, N.Y.

[21] Appl. No.: 642,159

[22] Filed: Dec. 18, 1975

[30] Foreign Application Priority Data

Dec. 23, 1974 Netherlands ................... 7416756

[51] Int. Cl.$^2$ ............................................. H05G 1/34
[52] U.S. Cl. .................................. 250/401; 250/322; 250/355; 250/409
[58] Field of Search ............... 250/322, 327, 354, 355, 250/401, 403, 409, 416; 315/106, 107

[56] References Cited

U.S. PATENT DOCUMENTS

| 3,558,885 | 1/1971 | Flemming | 250/354 X |
| 3,567,940 | 3/1971 | Lambert | 250/409 X |
| 3,783,286 | 1/1974 | Kremer | 250/409 X |

FOREIGN PATENT DOCUMENTS 834,815  5/1960  United Kingdom ................ 250/355

Primary Examiner—Eugene R. LaRoche
Attorney, Agent, or Firm—Frank R. Trifari

[57] ABSTRACT

The output dose behind the body to be examined in a scanning X-ray examination device is kept constant by controlling the incident dose. As a result, in comparison with known devices an examination can be performed quicker and with a smaller total radiation dose, and a better image of the absorption variations can be obtained.

9 Claims, 1 Drawing Figure

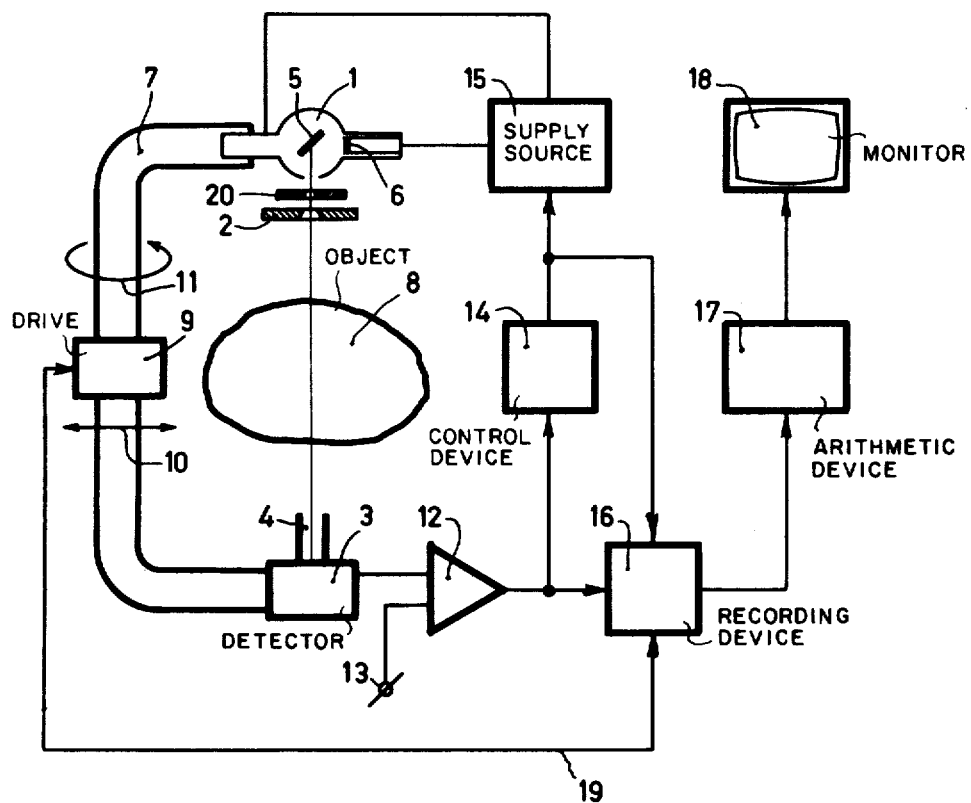

SCANNING X-RAY EXAMINATION APPARATUS

The invention relates to a device for measuring local absorption differences in a body, comprising a radiation source for generating a beam which irradiates the body, a scanning device, and a detector device for detecting emerging radiation.

A device of this kind is known, for example, from British Patent Specification No. 1,283,415. In a device described therein, a body, notably a part of the human body, is irradiated for medical examination by means of a radiation beam which scans the body. The intensity of the beam transmitted by the body is then measured and recorded in a series of different radiation directions. On the basis of these measuring data, the absorption of sub-elements of the body to be examined is determined by means of a calculating device. On the basis of these absorption data, any anomalies in the body are detected, localized and usually also qualified and quantisized. Known devices have a drawback in that a comparatively high dose of radiation must be applied for complete examination. The invention has for its object to mitigate this drawback, without adversely affecting the accuracy or the sensitivity of the device.

To this end, a device of the kind set forth according to the invention is characterized in that the detector device has coupled to it a control device for keeping, by means of the detector signal, the intensity of the emerging beam at least substantially constant during the entire scanning operation by adaptation of the locally incident dose.

Because the intensity of the emerging beam is constant within very narrow limits in a device according to the invention, optimum detection can be readily realized over the entire field to be scanned by optimum adaptation of the detector device to this intensity. The low dynamics of the detector device enable adjustment to a high sensitivity, without overdriving being liable to occur. When the quantity of radiation incident per unit of surface area is adapted to an emergent intensity which is favourable for the detection but minimum, overdosing with respect to the intensity desired for the measuring accuracy will not occur. As a result, the total quantity of radiation required for complete scanning is substantially reduced in comparison with known devices. Conversely, for the same total incident dose, an image of better quality can be realized on account of the locally constant value of the emergent intensity. Moreover, in a device according to the invention facilities for shielding direct radiation, i.e., radiation incident adjacent the body to be examined, can be dispensed with.

In a preferred embodiment of the device in accordance with the invention, the intensity of the incident beam is locally shaped for keeping the emergent intensity constant.

In a further preferred embodiment, the scanning speed of the incident beam is adapted for this purpose.

In a further preferred embodiment yet, utilizing a pulsating radiation source, the repetition frequency or the pulse-width of the incident beam is adapted for this purpose.

Some preferred embodiments of the device in accordance with the invention will be described in detail hereinafter with reference to the drawing.

The FIGURE is a diagrammatic view of a preferred embodiment in accordance with the invention.

The FIGURE shows a radiation source 1 with a diaphragm 2 and a detector 3 with a diaphragm 4 of a preferred embodiment of the device in accordance with the invention. The radiation source in this case consists of an X-ray tube comprising an anode 5 and a filament cathode 6. The source can alternatively comprise a natural radiator, for example, a gamma radiator, an electron radiator or a neutron radiator. The detector is adapted to the nature of the radiation to be used, and for electromagnetic radiation, such as X-radiation and gamma radiation, it comprises, for example, a scintillation crystal with a photomultiplier or a semiconductor detection element adapted to the said radiation, while for particle radiation it comprises a semiconductor detector adapted thereto. An object 8 to be examined can be positioned between the radiation source and the detector which are rigidly connected to each other by means of a bracket 7 in the embodiment shown.

The radiation source and the detector, driven together by a drive 9, can be moved with respect to the object to be examined, for example, as indicated by the arrows 10 for translation and the arrows 11 for rotation about the object 8. An output of the detector 3 is connected to an amplifier device 12, for example, an operational amplifier wherein a reference signal can be adjusted via a connection 13. The output of the amplifier is connected, via a control device 14 comprising, for example, a servomechanism, to a supply source 15 for the X-ray tube. During operation a reference signal is adjusted and during the entire exposure this reference signal is compared in the amplifier with the signal to be supplied by the detector. In the case of a fixed intensity of a radiation beam to be emitted by the radiation source, the detection signal will be varied only on account of a difference in absorption in the column of the body instantaneously present between the diaphragm 2 of the source and the diaphragm 4 of the detector. This difference in absorption is determined by the dimension of the object in the relevant column as well as by local differences in the absorption coefficient within the object.

A difference between the detection signal and the reference signal controls, via the control device 14, the supply source 15 for the X-ray tube. Variations in the detection signal caused by variations in the beam intensity of the radiation source can be compensated for, for example, by arranging a detector in a portion of the radiation beam which is not incident on the object. The reference signal can be related to a signal derived from this detector.

The supply source 15 controls, for example, the filament current for the cathode of the X-ray tube such that the radiation intensity emerging from the object is substantially constant.

The control signal can also be used for controlling the high voltage of the X-ray tube, so that a variation in the radiation beam occurs. The drawback that besides the intensity also the wavelength distribution of the X-radiation generated is then also varied, can be eliminated by using filter.

In a preferred embodiment, each time when the dose measured behind the object becomes equal to a dose given by the reference, for example, the high voltage of an X-ray tube as radiation source is switched off. It is thus achieved that the output signal behind the object is always constant, while the absorption variation in the object results in a variation in the pulse-width of the control signal. A deviation of the pulse-width variation of the control signal which is caused by fluctuations in the high voltage can be eliminated by means of a control circuit. In this control circuit the incident dose is measured, the emergent dose being kept constant, or rather the incident dose is derived from a measurement of the radiation delivered by the source which is not effectively used. The non-used dose is large with respect to the effectively used part of the radiation in the relevant devices, so that it is a suitable measure therefor in all practical circumstances. For measuring this dose, for example, a ring detector 20 (dosimeter) can be arranged on the source side of a diaphragm which limits the beam. It can be deduced from calculations that, if the incident dose is large with respect to the reference signal and hence with respect to the difference between the reference dose and the output dose, the absorption in the object is dependent only of the ratio between the incident dose, which is this always accurately measured, and a dose which is given by the reference signal and which is exactly adjusted. Fluctuations in the radiation output of the source do not have an adverse effect on the measuring accuracy, i.e., the pulse-width ratios of the control signal to be used for furthe processing. Using the control signal, the electron beam which releases the X-rays in the X-ray tube can also be deflected or defocussed such that a variation in the intensity of the emitted X-ray beam occurs at least in the part thereof which is to be effectively used. When a comparatively narrow beam is used, the inhomogeneity in the intensit;y distribution across the beam section is negligibly small. For the defocussing or deflection of the electron beam an additional electrode or electrode system can be arranged in the X-ray tube, in this case preferably a grid-controlled tube. Discrepancies in the measurement by means of the said second detector for the unimpeded beam can be readily corrected by way of a calibration measurement. The latter method has the advantage over the previously described methods that substantially no delay occurs in the control. When the X-ray beam is adapted by filament current variation and high voltage variation, such a delay can definitely occur. For the proper operation of the device in accordance with the invention, however, this is not objectionable. Fast, comparatively small variations will then occur in the output signal, but these variations will not have a significant effect on the radiation dose. From these fast variations a correction signal can be derived whereby the control signal can be corrected such that for the further processing of this signal (for the absorption determinations) this disturbance is compensated for.

The control signal is a measure for the absorption occurring and is applied to a register 16 for recording and further processing. Using an arithmetic device 17, the absorption of sub-elements of the body to be examined is calculated therefrom in known manner. The results of the calculation can be displayed on a monitor 18. The density distribution of a section of the body is preferably displayed on the monitor in a mosaic pattern. The mosaic pattern is then formed, for example, by squares having small edges (with respect to the body to be examined) of, for example, 3 millimeters, the section thickness being, for example, 8 millimeters. A coupling 19 between the scanning mechanism and the recording device determines the position within the body of the section of the body to be displayed.

In a further preferred embodiment of the device in accordance with the invention, the scanning speed of the device is controlled by means of the control signal. A constant output intensity can thus also be realized. The intensity of the incident beam is then constant across the entire field to be scanned, but by variation of the duration of the scanning of a sub-traject the applied dose is still varied. Thus, a saving is again realized as regards total dose and time required. The drawback of a possible delay in the control can be eliminated in the same manner as described already for fast variations. This method is particularly suitable for use in devices wherein a source which is difficult to control, for example, a radioactive specimen, is used.

In a device utilizing a pulsating source, the control signal can be used for influencing the frequency of the pulses or the pulse-width. A device of this kind is particularly attractive for the examination of periodically moving parts of the body, such as the heart. When the scanning pattern and the pulse action of the source are adapted to each other, the movement of the pulsating part of the body can be eliminated, so that scanning in synchronism with the heart beat is realized. In this preferred embodiment it is advantageous to use the simultaneous scanning device described in the said British Patent Specification No. 1,283,415, that is to say the device wherein use is made of a diverging beam which simultaneously irradiates a section of the body, a scanning motion being preformed only for a change over to a subsequent section.

What is claimed is:

1. A device for measuring local radiation absorption differences in a body, comprising:
   means for scanning a body with a locally incident radiation beam;
   means for detecting the resulting radiation intensity emerging from the body;
   control means responsive to said detecting means for automatically varying the locally incident dose of radiation so as to keep the detected intensity substantially constant during the entire scanning of the body; and
   means responsive to said control means for deriving a signal indicative of the locally incident radiation dose, said signal being a measure of local radiation absorption in the body.

2. A device as claimed in claim 1, characterized in that the control means is coupled to a supply source for a radiation source comprising a thermal cathode, and comprises a filament current control system controlled by the detecting means.

3. A device as claimed in claim 1, characterized in that the control means is coupled to a supply source for a high voltage radiation source and comprises a high voltage control system which is controlled by the detecting means.

4. A device as claimed in claim 1, characterized in that the scanning means is provided with electron-optical elements for generating and controlling a beam of charged particles, the control means comprising an excitation source, controlled by the detecting means, for a suitable electron-optical element.

5. A device as claimed in claim 1, characterized in that the control means is coupled to an on-off switch for a radiation source, the control means being responsive to pulse-width ratios.

6. A device as claimed in claim 1, characterized in that the control means is coupled to the scanning means and comprises a mechanism for controlling the scanning speed in dependence of detected radiation intensity.

7. A device as claimed in claim 1, and further comprising a radiation source designed for pulsating excitation, the detecting means controlling a control device for the repetition frequency or the pulse-width of the excitation.

8. A device as claimed in claim 7, characterized in that there is provided a synchronisation device for the matching of the excitation of the radiation source and the scanning.

9. A device as claimed in claim 8, characterized in that the phase of the excitation of the radiation source is coupled to the scanning by means of a synchronisation pulse which is to be additionally applied.

* * * * *